United States Patent [19]
Clatch

[11] Patent Number: 6,165,739
[45] Date of Patent: Dec. 26, 2000

[54] MULTIPLE SIMULTANEOUS TESTING MEDIA

[75] Inventor: Richard J. Clatch, Glenview, Ill.

[73] Assignee: CompuCyte Corporation, Cambridge, Mass.

[21] Appl. No.: 09/372,115

[22] Filed: Aug. 20, 1999

Related U.S. Application Data

[63] Continuation of application No. 09/120,562, Jul. 22, 1998, which is a continuation of application No. 08/614,649, Mar. 13, 1996, Pat. No. 5,889,913.

[51] Int. Cl.$^7$ .............................. C12Q 1/02; C12M 1/00
[52] U.S. Cl. .................... 435/29; 435/283.1; 435/286.5; 435/287.1; 422/50; 372/43
[58] Field of Search ................... 435/29, 283.1, 435/286.5, 287.1; 422/50; 372/43

[56] References Cited

U.S. PATENT DOCUMENTS

| | | | |
|---|---|---|---|
| 3,799,742 | 3/1974 | Coleman | 435/29 |
| 4,171,866 | 10/1979 | Tolles | 435/29 |
| 4,665,020 | 5/1987 | Saunders | 435/283.1 |
| 4,665,553 | 5/1987 | Gershman et al. | 435/29 |
| 4,761,381 | 8/1988 | Blatt et al. | 435/29 |
| 4,963,498 | 10/1990 | Hillman et al. | 435/29 |
| 5,004,584 | 4/1991 | Rayman | 435/29 |
| 5,019,351 | 5/1991 | Schulz | 435/29 |
| 5,072,382 | 12/1991 | Kamentsky | 435/29 |
| 5,144,139 | 9/1992 | Hillman et al. | 435/29 |
| 5,147,606 | 9/1992 | Charlton et al. | 435/29 |
| 5,164,598 | 11/1992 | Hillman et al. | 435/29 |
| 5,227,290 | 7/1993 | Pocock | 435/7.1 |
| 5,278,048 | 1/1994 | Parce et al. | 435/29 |
| 5,296,375 | 3/1994 | Kricka et al. | 435/29 |
| 5,302,348 | 4/1994 | Cusack et al. | 435/29 |
| 5,401,637 | 3/1995 | Pocock | 435/7.1 |
| 5,409,832 | 4/1995 | Pocock | 435/287 |
| 5,534,226 | 7/1996 | Gavin et al. | 435/29 |
| 5,547,849 | 8/1996 | Baer et al. | 435/29 |
| 5,548,661 | 8/1996 | Price et al. | 435/29 |
| 5,608,519 | 3/1997 | Gourley et al. | 435/29 |
| 5,731,212 | 3/1998 | Gavin et al. | 435/29 |
| 5,793,485 | 8/1998 | Gourley | 435/29 |
| 5,885,840 | 3/1999 | Kamentsky et al. | 435/29 |
| 5,889,913 | 3/1999 | Tohyama et al. | 372/43 |
| 6,007,775 | 12/1999 | Yager | 422/57 |

OTHER PUBLICATIONS

Clatch et al., "Five–Color Immunophenotyping Plus DNA Content Analysis by Laser Scanning Cytometry," Cytometry 34:36–38 (1998). Month not available.

Clatch et al., "Immunophenotypic Analysis of Hematologic Malignancy by Laser Scanning Cytometry," American Journal of Clinical Pathology 105(6): 744–755 (1996). Month not available.

Clatch et al., "Multiparameter Immunophenotypic Analysis of Fine Needle Aspiration Biopsies and Other Hematologic Specimens by Laser Scanning Cytometry," Acta Cytologica 41:109–122 (1997). Month not available.

(List continued on next page.)

*Primary Examiner*—Louise N. Leary
*Attorney, Agent, or Firm*—Testa, Hurwitz & Thibeault LLP

[57] ABSTRACT

A stationary testing media device made of a glass or plastic plate and conveniently a microscope slide, wherein multiple simultaneous tests are conducted on a single multifurcated testing sample. The plate or slide is partitioned into two or more testing zones with each of the zones having been preferably pre-loaded with a stable test reactant. The testing zones are physically separated from one another but are connected, with a fluid flow connection, to a single sample reservoir which simultaneously feeds, such as by capillary action, each of the testing zones with a test portion of the testing sample. The testing zones retain the individual portions for a time sufficient to effect the individual zone reactions with pre-loaded reagents. An optional outflow reservoir is utilized to capture excess sample flow and flushing fluids. Cell samples undergoing laser scanning cytometry are able to be simultaneously reacted, such as with varying fluorescent dyes, to provide a series of test profiles with a single sample and testing procedure.

4 Claims, 4 Drawing Sheets

OTHER PUBLICATIONS

Clatch et al., "Multiparameter Analysis of DNA Content and Cytokeratin Expression in Breast Carcinoma by Laser Scanning Cytometry," Arch. Pathol. Lab. Med. 121: 585–592 (1997). Month not available.

Eric Scientific, Pamphlet, "The SuperCell™ Slide," 2 pages (undated).

Gorczyca et al., "Laser Scanning Cytometric Analysis of Cyclin B1 in Primary Human Malignancies," Modern Pathology 10(5): 457–62 (1997). Month not available.

Gorczyca et al., "Laser Scanning Cytometry in Pathology of Solid Tumors," Acta Cytologica 41: 98–108 (1997). Month not available.

Kamentsky et al., "Slide–Based Laser Scanning Cytometry," Acta Cytologica 41: 123–143 (1997). Month not available.

Kamentsky et al., "Microscope–Based Multiparameter Laser Scanning Cytometer Yielding Data Comparable to Flow Cytometry Data," Cytometry 12: 381–387 (1991). Month not available.

Knowles, "Organization and Operation of a Hematopathology Laboratory," In: Neoplastic Hematopathology, pp. 323–366 (1992). Month not available.

Martin–Reay et al., "Evaluation of a New Slide–based Laser Scanning Cytometer for DNA Analysis of Tumors," American Journal of Clinical Pathology 102: 432–38 (1994). Month not available.

Sasaki et al., "DNA Ploidy Analysis by Laser Scanning Cytometry (LSC) in Colorectal Cancers and Comparison With Flow Cytometry," Cytometry 23; 106–109 (1996). Month not available.

"StatSpin Cytofuge" Pamphlet, 4 pages (undated).

Sun, "Color Atlas–Text of Flow Cytometric Analysis of Hematologic Neoplasms," Igaku–Shoin Medical Publishers, Inc., pp. 3–8; 18–25; and 206–211 (1993). Month not available.

Willman, "Flow Cytometric Analysis of Hematologic Specimens," In: Neoplastic Hematopathology, pp. 169–195 (1992). Month not available.

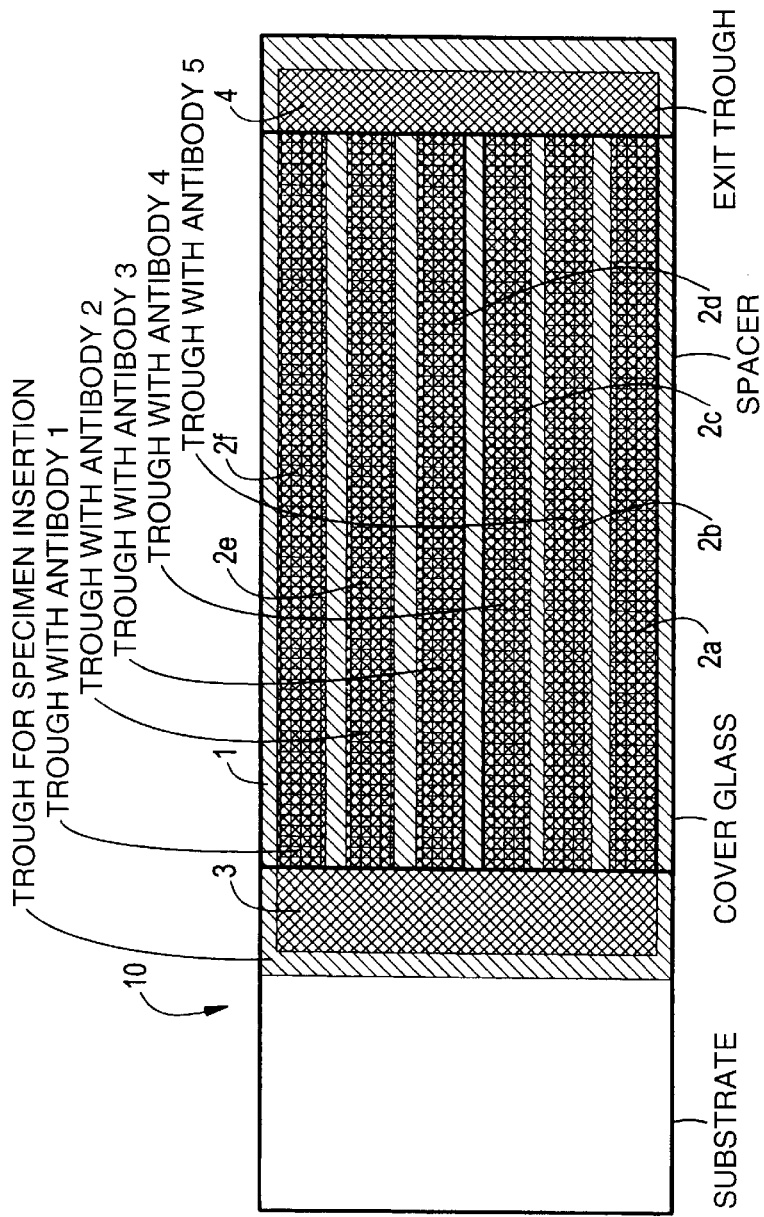
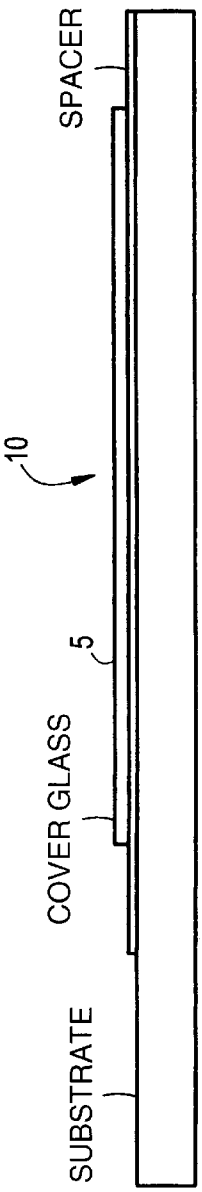
FIG. 1
FIG. 2

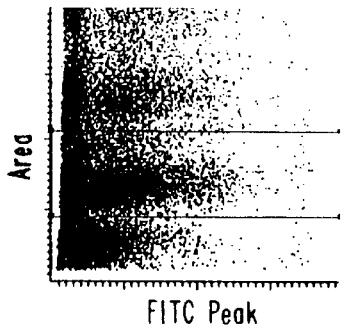
FIG.5A
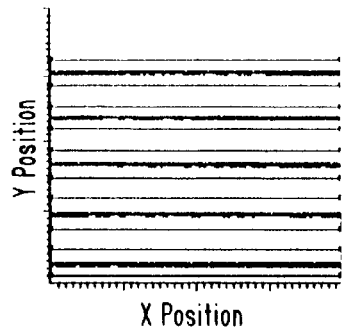
FIG.5B
FIG.5C       FIG.5D       FIG.5E
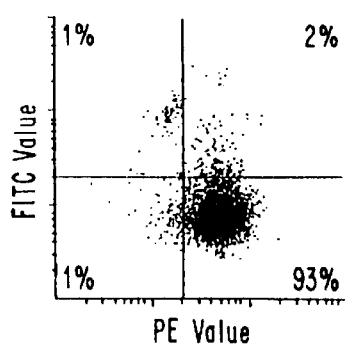
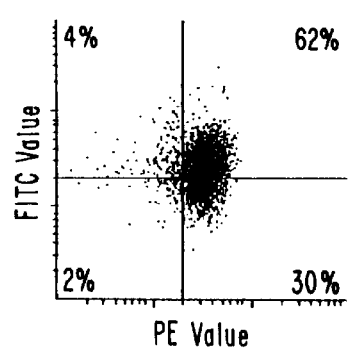
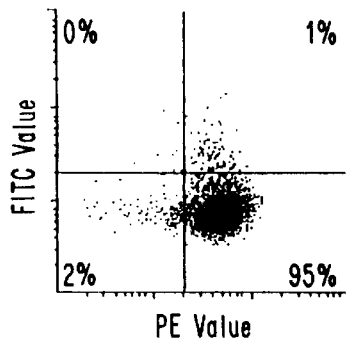
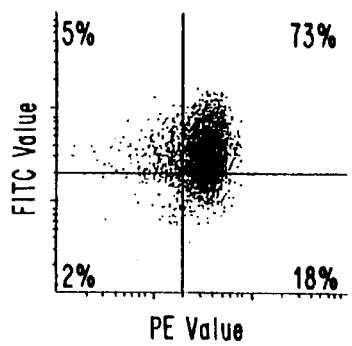
FIG.5F       FIG.5G

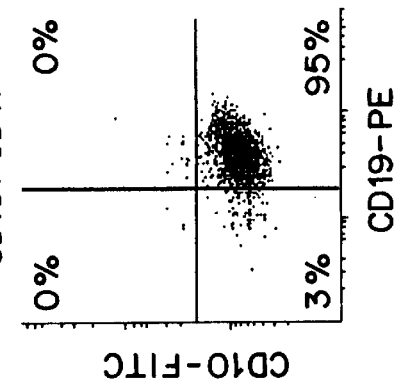
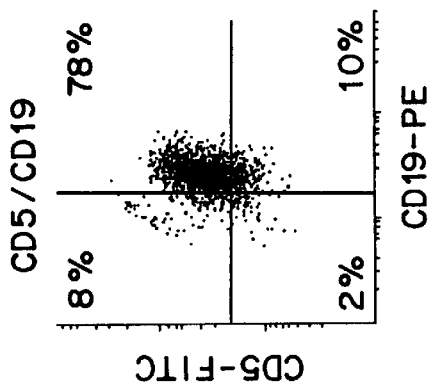
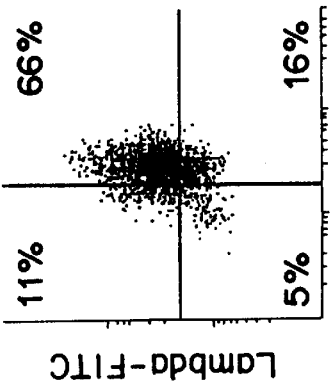
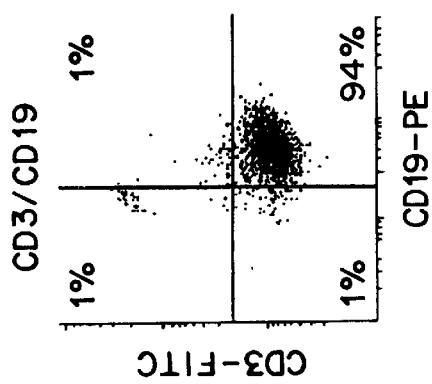
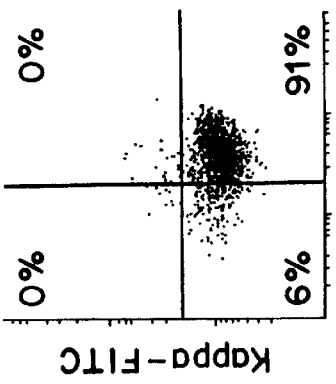

MULTIPLE SIMULTANEOUS TESTING MEDIA

This application is a continuation of U.S. Ser. No. 09/120,562, filed Jul. 22, 1998, which is a continuation of and claims priority to U.S. Ser. No. 08/614,469, filed Mar. 13, 1996, now U.S. Pat. No. 5,889,913.

FIELD OF THE INVENTION

This invention relates to diagnostic testing procedures and testing vehicles such as glass or plastic plates and particularly to microscope slides used in laser scanning cytometry.

BACKGROUND OF THE INVENTION

Microscope diagnostic characterization of hematologic neoplasms is increasingly dependent on immunophenotypic analysis, often performed by flow cytometry. Immunophenotyping by flow cytometry provides objective data that is necessary for the subclassification of leukemia and lymphoma, and that can often definitely establish or exclude a diagnosis of malignancy in seemingly borderline cases. Immunophenotyping of peripheral blood leukocyte subsets is also an important laboratory indicator for patients infected with the human immunodeficiency virus (HIV) that causes the acquired immunodeficiency syndrome (AIDS). Flow cytometers are used routinely to provide dual antibody profiles using patient blood and other specimens such as tissue biopsies. Each set of dual measurement requires a separate tube containing cells treated with two antibodies. Each tube is independently run on the flow cytometer and the results of all measurements are combined on a report. Although it is possible to measure as many as four different antibodies at the same time on each cell with a flow cytometer, this is technically difficult and expensive. Therefore, multiple aliquots of dual antibodies are more commonly utilized.

Drawbacks of flow cytometry include relatively large specimen size requirements and the inability to microscopically examine the cells being studied. Furthermore, in order to normally accomplish multi-parameter immunophenotyping (greater than four immunofluorescent antibodies per specimen), flow cytometric analysis requires that separate subsets of a single specimen be manually or robotically placed within the flow cytometer and analyzed separately.

Until now, alternatives to flow cytometry have been few, including only immunohistochemical methods that suffer from a lack of automation and objectivity, and that generally compromise the number of antigens that can be analyzed.

A device, referred to as a laser scanning cytometer, available from CompuCyte Corp. (under the trademark "LSC", as described in U.S. Pat. No. 5,072,382, the disclosure of which is incorporated herein by reference thereto), has been recently developed which provides an alternative to flow cytometric immunophenotyping, and offers several unique advantages. Similar to flow cytometry, laser scanning cytometry provides objective automated, multi-color analyses of hematologic cell suspensions, stained by using conventional immunofluorescent techniques. However, laser scanning cytometry also allows for the visual examination of individual cells both during and after analysis, and makes possible the analysis of very small diagnostic samples, such as those obtained via fine needle aspiration biopsy. This is true primarily because for laser scanning cytometry, the specimens are analyzed on a static surface (such as a glass microscope slide) rather than within a fluid stream as with flow cytometry. An added advantage and the principal idea behind the present invention is that for laser scanning cytometry true multi-parameter immunophenotyping of a single specimen (or even multiple specimens) is possible using only a single glass microscope slide or other vehicle to load the specimen into the laser scanning cytometer.

Preparation of a specimen for immunophenotypic analysis is performed by reacting aliquoted subsets of that specimen (typically constituting a suspension of purified hemopoietic or lymphoreticular cells) with various mixtures of fluorochrome-labelled antibodies. After this reaction, the aliquoted subsets are washed and analyzed individually via flow cytometry or laser scanning cytometry. Typically each aliquot is reacted simultaneously with a mixture of up to four different antibodies labelled with different fluorochromes. This is possible because of differences in the spectral characteristics of the fluorochromes utilized and because the instrumentation of flow cytometer or the laser scanning cytometer is designed to simultaneously but discretely assay emitted light from such fluorochromes. Because of the cost of producing different antibodies labeled with various fluorochromes and the cost and complexity of instrumentation necessary for the assay, individual aliquoted subsets of a single specimen are usually simultaneously reacted with only two or three different antibodies. However, modern immunophenotypic analysis usually requires assessment of multiple (usually 5 to 15) different antigens, and it is often clinically necessary or desirable to assess a single particular antigen in the context of multiple different other antigens. Therefore, specimens are presently aliquoted and reacted with multiple mixtures of various fluorochrome-labelled antibodies to is assess the expression of the corresponding antigens and their relationships with one another.

For testing of the multiple mixtures, at least three manufacturers sell slides with multiple compartments or devices which can create multiple compartments. These do not, however, provide means for generating an assay and they also require separate aliquot samples for each of the compartments or chambers.

SUMMARY OF THE INVENTION

It is an object of the present invention to provide a stationary testing media embodied in a testing plate made of glass or plastic and conveniently embodied in a microscope slide, wherein multiple simultaneous tests are conducted on a single self-multifurcated testing sample.

It is a further object of the present invention to provide such media for use with laser scanning cytometry devices.

These and other objects, features and advantages of the present invention will become more evident from the following discussion and drawings in which:

SHORT DESCRIPTION OF THE DRAWINGS

FIG. 1 is a top view of a multi-chambered slide of the present invention;

FIG. 2 is a side view of the slide of FIG. 1;

Figure 3:
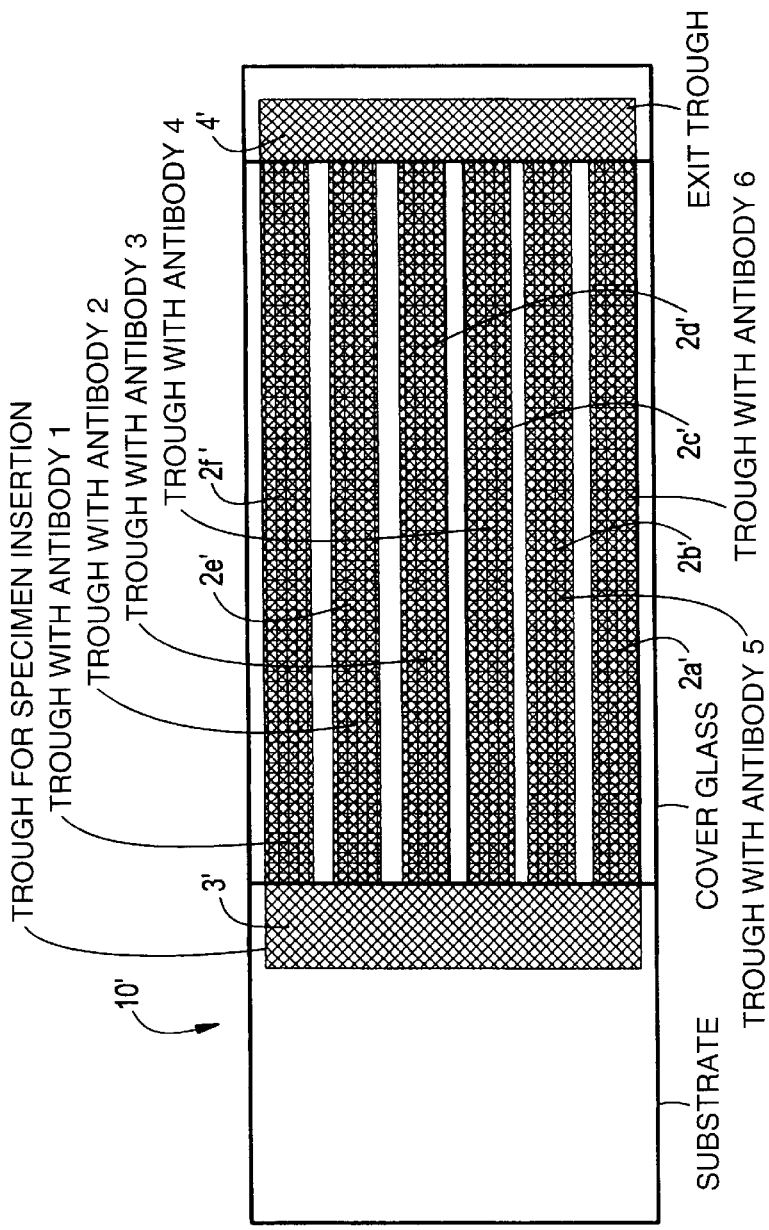
FIG. 3 is a top view of a second embodiment of a multi-chambered slide of the present invention.
Figure 4:
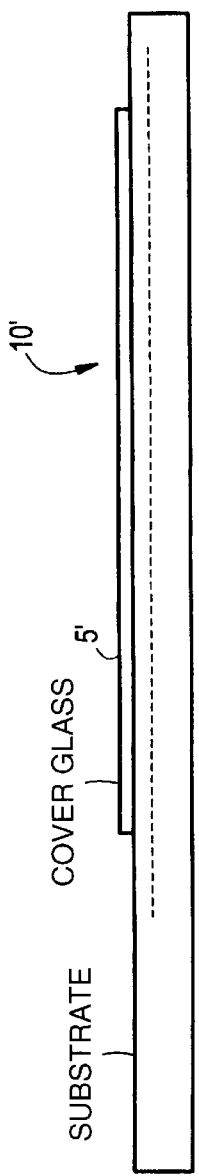
FIG. 4 is a side view of the slide of FIG. 3.

FIGS. 5a–g are multiple profile test results from a single sample, obtained by using the multi-chambered slide of FIGS. 1 and 2.

FIGS. 6a–e are test results obtained by using prior art individual test sample runs with single tube assays.

DETAILED DESCRIPTION OF THE INVENTION

Generally the present invention comprises a multiple simultaneous testing media device and testing method, which utilizes the ability of a laser scanning cytometer to geographically locate and distinguish different regions of one or more specimens constituting a single analysis. The preferred embodiment of the device comprises a substrate such as a glass or plastic plate which is partitioned into two or more testing chamber zones with each of the zones having been pre-loaded with a stable test reactant. The testing zones are physically separated from one another but are connected, with a fluid flow connection, to a single sample reservoir which simultaneously feeds, such as by capillary action, each of the testing zones with a test portion of the testing sample. The testing zones retain the individual portions for a time sufficient to effect the individual zone reactions with pre-loaded reagents. An optional outflow reservoir is utilized to capture excess sample flow and flushing fluids. In less preferred embodiments, the individual test reactants are separately loaded into the testing chamber zones together with the individual test portions samples or thereafter into the test portions, by means such as pipetting.

The present invention further comprises a method of conducting at least two simultaneous tests with a laser scanning cytometer, with a single test sample on a single glass or plastic plate such as a microscope slide, said method comprising the steps of:

a. providing the plate or slide with a test sample reservoir and at least two separated sample portion troughs in fluid connection with the reservoir;

b. providing each of the sample troughs with a stable reactant for a test sample, preferably prior to introduction of the test sample;

c. placing a fluid test sample in said reservoir wherein fluid connection means causes portions of the test sample to flow into each of the at least two separated sample portion troughs;

d. maintaining sufficient cells in each of the portions in said portion troughs for a time sufficient for the cells to react with the stable reactant within the individual portion troughs; and e. removing excess reactant whereby test results can be meaningfully obtained by the laser scanning cytometer with minimized background noise.

Cell samples undergoing laser scanning cytometry are able to be simultaneously reacted, such as with various fluorescent dyes, to provide a series of test profiles with a single sample and testing procedure. The device comprises a loading vehicle for laser scanning cytometry in which different geographic regions of the loading vehicle correlate with different test conditions. With respect to immunophenotypic analysis, this provides for multiple simultaneous reactions of one or more samples with multiple mixtures of fluorochrome-labelled antibodies. The vehicle is then loaded into a laser scanning cytometer; and, by means of a single comprehensive analysis of the material on the loading vehicle, multiple reaction mixtures or "geographic aliquots" of one or more specimens are assayed automatically.

Various embodiments of the present invention, relating to immunophenotypic analysis, can be broadly divided into two groups. One group relies on cells becoming affixed to the loading device whereas the other relies on the cells not becoming affixed. Affixation of lymphoreticular cells to a glass or plastic surface within the loading device is largely a function of cell type, the physical characteristics of the surface, and the manner in which the cells and surface are brought together.

Embodiment of Surface Affixed Cells:

Thus, in a preferred embodiment, cells become affixed to a surface within the loading device, which is essentially a modified glass or plastic plate or conveniently a microscope slide. The plate is divided into several geographic regions either horizontally or vertically. It is preferred to create regions oriented horizontally (x-axis) in the device, in order to take greatest advantage of the direction of movement of the stage of the laser scanning cytometer, but vertically (y-axis) oriented regions work equally well.

With a typical slide it is preferred to create up to six distinct regions, because this nicely correlates to different analytical groups necessary for complete immunophenotyping of leukemia or lymphoma specimens as hematopathology is practiced today. However, the absolute number of regions created is essentially arbitrary.

A simple, yet effective manner of creating the six horizontally (x-axis) oriented regions, as a demonstration of the effectiveness of the device, is by means of very thin (e.g., 1 mm) strips of polymeric based double-stick adhesive tape, essentially inert to standard test specimens. Two or three thicknesses of conventional Scotch® brand Double Stick Tape works exceptionally well. Since a glass microscope slide is approximately 25 mm in vertical (y axis) dimension, six regions, i.e., chamber zones, are created with each having an approximate width of 2.5 mm. The regions are formed with 10 mm length×1 mm width strips of tape being placed on the glass slide, as region boundaries. The regions are covered with a 24×40 mm glass coverslip to create six geometrically separate open ended capillary gap chambers within a single loading device. At one of the two open ends of the capillary gap chambers, a trough or specimen reservoir, is formed whereby fluids placed in the trough simultaneously enter all six chambers. In a preferred embodiment the loading device is unitarily molded out of plastic, or assembled from plastic and glass.

An advantage of the device of the present invention is that fluorochrome-labelled antibodies (singly, in pairs, or in triplets) can be preloaded into the chambers, with each chamber holding a different antibody combination. These antibodies are most advantageously preloaded prior to sale of the device, and may be either in a stable liquid or dried state. Antibodies predried within separate chambers prior to coverslipping have maintained their immunologic and fluorescent activity to a significant degree.

The method of using the device for immunophenotyping comprises initial loading of a single aliquot of a relatively small specimen (approximately 300 $\mu$l containing approximately 200,000 cells) into the trough, which automatically fills all six chambers completely (approximately 50 $\mu$l each). The suspension of cells mixes with the antibodies specific to each chamber and is allowed to react for approximately 30 minutes at room temperature. If untreated glass microscope slides are used to make the device, more than 90% of the cells will have settled and become affixed to the slide surface at the end of this time. Thereafter approximately 1 ml of saline wash solution is placed into the trough and either allowed to drain through the six chambers by gravity or by means of a fixed volume of absorbent material placed at the exit end of the chambers. If an unlimited amount of absorbent material is available, the chambers will however be unacceptably drained dry. With the aforementioned procedure, more than 90% of the cells remain affixed to the surface of the loading vehicle for subsequent immunophenotypic analysis.

Embodiment of Non-Surfaced Affixed Cells:

Immunophenotypic analysis using a geographically partitioned loading device wherein the cells do not become affixed to a surface within the device has some advantages as compared with the embodiment described above but, may also have greater disadvantages and is less preferred. The loading device for this embodiment is similarly created using a glass microscope slide, double stick tape, and a coverslip.

Glass slides treated for immunohistochemistry have an interesting property that lymphoreticular cells in general do not become affixed to them. As before, horizontally (x-axis) oriented capillary chambers are created using thin strips of two or three thicknesses of double stick tape. However, for this embodiment, the tape is cut into shapes slightly more complex than simple strips, each capillary chamber is itself partitioned into two regions, one quite small (5 $\mu$l volume) at the entrance end of the chamber and another relatively large (45 $\mu$l volume) in the middle and at the exit end of the chamber. The two regions of each chamber are connected by only a small gap through which cells and diluent can flow only if sufficient volume pressure is applied to the loading end of the chamber. The different antibodies may be pre-loaded into the 5 $\mu$l regions of the chambers and remain in liquid or dry state as described above.

A trough (or reservoir) similar to that described above is utilized to automatically load specimens into each of the six chambers. However, in this embodiment, the immunologic reactions are occurring in only 5 $\mu$l of volume and so the quantity of antibody necessary is far less (1/10th of that as described above) and the specimen must be 10 times more concentrated but in 1/10th the volume. Thus, for example, 200,000 cells would be loaded in only 30 $\mu$l of diluent. After the reactions are complete (after approximately 30 minutes at room temperature), the trough is filled with 270 $\mu$l of diluent, which is sufficient to force the cells from the 5 $\mu$l region of each chamber into the larger 45 $\mu$l region. Although not a true wash, this constitutes a 1/10 dilution of unbound antibody, which is sufficient to reduce background fluorescence levels to an acceptable level for analysis.

An advantage of this embodiment is that all reagents remain completely within the device and do not need to be drained or absorbed from the exit end of the chambers. An additional advantage is the savings with respect to quantities of antibody used.

In order to obtain advantages of both embodiments, a device having two region chambers, as described is made with a non-sticky surface within the 5 $\mu$l chamber and a sticky surface within the 45 $\mu$l chamber.

In a further highly preferred embodiment (common to both the above enumerated cell type embodiments), the dimensions of the troughs or chambers are controlled to provide known volumes via known (or determinable) chamber depths, in order to ascertain characteristics of the separately tested and laser scanned samples in each of the chambers. The LSC™ laser scanning cytometer containes software which counts the various cells in each region of a scattergram as well as cells displayed on the scattergram and is able to provide the ratio of cells counted in a region to all cells displayed on the scattergram. It is a very useful feature for the cytometer to provide both absolute counts of numbers of each cell type found per cubic millimeter, as well as percentages of each cell type relative to total cells measured. In order to provide such absolute counts and percentages, the counts are based on measurement of a known specimen volume. Thus, an initial specimen is precisely diluted prior to placement on the loading vehicle and the cytometer determines the volume of each testing chamber to obtain precise volumetric count. In order for the cytometer to determine the chamber volume (completely filled by the specimen), the individual chamber depth (distance from substrate to coverslip or coverglass is made with a known fixed thickness). The laser scanning cytometer is capable of scanning over a fixed known area by fixing the extent of the laser scan that is digitized and keeping track of the number of known step size steps that are moved in the perpendicular direction to complete the assay. Since the area scanned, the specimen dilution factor, and the loading vehicle chamber thickness or depth are known, the assay volume can be calculated, with the absolute count being thereby related to the undiluted absolute count, by the dilution factor.

Alternatively, the cytometer itself is modified to measure the depth of the chamber prior to scanning the specimen. A manner of effecting such measurement is by automatically focussing on indicia printed on the two inner surfaces which define the chamber depth and measuring the distance between the focus points.

DETAILED DESCRIPTION OF THE DRAWINGS AND THE PREFERRED EMBODIMENT

FIG. 1 is a diagram of the Loading Vehicle (LV) 10 (shown as a microscope slide) made by applying double stick tape to a standard microscope slide in the areas 1, as spacer elements. Application of the tape in this pattern creates a set of horizontal chambers 2a–f, each connected to a specimen insertion trough (specimen reservoir) 3 and an exit trough 4. For effective use, four $\mu$l of a mixture of two antibodies are added to each horizontal chamber, which antibodies are specific to proteins on the surface or within human white blood cells. As described in the subsequent example herein, One of these antibodies CD19, conjugated to the dye phycoeritherin (PE), is used in all chambers (five of the chambers are described as being actually used in the example). All of the other antibodies are conjugated to the dye fluorescein isothiocyanate (FITC). From the bottom chamber 2a, the second antibody added to each successive chamber (2a–2e) is specific for CD3, CD5, CD10, Kappa and Lambda. In use, the antibodies are allowed to dry to a gel at which time a cover slip glass 5 (more clearly seen in FIG. 2) is applied over the double stick tape.

FIG. 3 shows an alternative loading vehicle 10' with imbedded chambers 2a'–f', in which the chambers are formed within the substrate rather than with spacer tape 1 as in FIGS. 1–2.

After data acquisition, the cells are stained within the single loading device of FIGS. 1 and 2, for microscopic examination. Approximately 500 $\mu$l of the desired staining solutions are placed in succession into the trough in the loading vehicle and allowing them to drain through by gravity or by being drawn into absorbent material at the exit end of the capillary chamber. More than 90% of the cells are retained within the loading device, in part aided by the fact that most staining procedures for light microscopy begin with an organic solvent fixation. Thus, one single specimen can be used for immunophenotyping and subsequent microscopic examination making full use of the LSC's capability to relocalize for visualization only cells that meet particular user-defined criteria of fluorescence, light scatter, size, etc.

The following examples illustrate the simultaneous testing regimen of the present invention as compared to the individual testing of the same specimens. It is understood that such examples are for illustrative purposes only and that details contained therein are not to be construed as limitations on the present invention.

EXAMPLE 1

In a testing regimen, the testing vehicle of partitioned microscope slide 10 of FIGS. 1 and 2 is utilized, with 240

μl of a phosphate buffered saline suspension of human benign lymphoid cells from a hyperplastic tonsil being pipetted into specimen trough 3 therein. After 15 minutes, phosphate buffered saline is added to the insertion trough and an exit trough 4 is wicked, in order to wash the cells now adhered to the microscope slide.

The slide is placed on the stage of an LSC™ (laser scanning cytometer from CompuCyte Corp.) scanning device and the protocol of the device is set to make it scan a pattern consisting of a set of single strips each centered along each horizontal chamber. The LSC device images a 5 micron diameter laser beam on the slide surface in a scan pattern which consists of a series of vertical lines approximately 300 microns in length along a strip which, in this case, is 50 mm long. As each cell is encountered by the laser beam both scatter and fluorescence emissions from dyes in the cell are detected by sensors. The LSC is set to measure three properties of each cell encountered by the laser beam, forward angle light scatter (FALS) used to detect the presence of and contour or delineate each cell, green fluorescence to measure FITC, and red fluorescence to measure PE.

Results of the run of the specimen are shown in FIGS. 5a–g. FIG. 5a provides the area versus FITC peak for all cells used to gate single cells. FIG. 5b is a map of the loading vehicle slide showing the cells in each lane or chamber. FIGS. 5c–g are a series of scattergrams which display dots representing each cell measured, the coordinates of which are proportional to each of two measurements. The first scattergram (FIG. 5a) of the area of each cell as measured using FALS and peak FITC fluorescence is used to isolate single cell events from multiple cell events and debris. Only cells which have coordinates within the single cell gate area are presented as input to the other displays. The second scattergram (FIG. 5b), in which the X Y position of each cell is plotted, is used to gate all of the cells measured into five different scattergrams (FIGS. 5c–g), each one of which now obtains data from a single different scan strip corresponding to each horizontal chamber of the vehicle of FIG. 1. Each of the scattergrams (5c–g), which use logarithmic scales, show a plot of each cell's FITC versus PE fluorescence resulting from the antibody reactions in its corresponding chamber (CD19 in each chamber with CD3, CD5, CD10, Kappa and Lambda in each of FIGS. 5c–g, respectively). Each of these scattergrams are divided into four quadrants. The number of cells in each quadrant can be tabulated to obtain a numerical value for the number of cells positive or negative for each combination of two antibodies. These values are printable on a report, thereby providing useful diagnostic information to a clinician.

In comparison to the results of the above tests, the following Example illustrates results obtained with prior art individual testing methods, wherein the results are essentially indistinguishable from that of the present invention.

EXAMPLE 2

A portion of a specimen from the same source as that used in Example 1 is divided into aliquots in microtiter tubes, with each aliquot being reacted with a different pair of fluorochrome-labelled antibodies (the same pairs as in Example 1). The cells are then washed by centrifugation and a drop from each microtiter tube is placed on each of separate slides, with data being acquired with the LSC scanning device for each slide aliquot individually.

Scattergrams (FIGS. 6a–g) are generated individually using each specimen placed onto a single microscope slide, as described above, after reacting with the five antibody pairs. The five sets of scattergrams from Example 1 and Example 2 are substantially identical.

It is understood that there are many other means of reacting affixed cells with immunofluorescent reagents in ways that create geographic partitioning. Thus, for example, affixation of the cells can be done through the use of a cytospin apparatus. Thereafter, different geographic regions of this layer of cells are reacted with multiple different mixtures of fluorochrome-labelled antibodies. The means of applying the antibodies in the correct geographic locations may vary from complex multi-channel fluidics systems to manual pipetting to systems utilizing a porous or sponge-like material possibly pre-impregnated with the antibody mixtures. The use of pre-impregnated pads or some other potentially disposable means of delivering the antibody pairs or groups to a layer of affixed cells is preferred in order to eliminate time consuming and technically demanding pipetting, as well as to automatically create geographic checkerboards of different antibody mixtures. As with the preloaded devices described above, such pre-impregnated pads may be designed to contain antibody panels specific for different clinical differential diagnoses, thereby reducing waste for hospital laboratories.

What is claimed is:

1. A method of conducting at least two simultaneous tests on a single test sample with a laser scanning cytometer, wherein the single test sample is located on a single glass or plastic plate, said method comprising the steps of:
   a. providing the plate with a test sample reservoir and at least two separated sample portion troughs in fluid connection with the reservoir;
   b. providing each of the sample troughs with a stable reactant for a test sample, with said stable reactant being different in each sample trough in order to perform different tests on the test sample at the same time, and with said different stable reactants being provided in the sample troughs either before or after the placing of a fluid test sample in the respective sample troughs;
   c. placing a fluid test sample containing cells in said reservoir wherein fluid connection means causes portions of the test sample to flow into each of the at least two separated sample portion troughs;
   d. maintaining sufficient cells in each of the portion troughs for a time sufficient for the cells to react with the stable reactant within the individual portion troughs; and
   e. removing excess reactant cells and scanning each of the portion troughs, containing cells reacted with the stable reactant, with a laser scanning cytometer, whereby test results can be meaningfully obtained by the laser scanning cytometer with minimized background noise.

2. The method of claim 1, wherein depth of each of the sample portion troughs is of predetermined dimensions and wherein the method further comprises the steps of:
   i) precisely diluting the fluid test sample prior to placement in said reservoir;
   ii) performing an assay by scanning the fluid test samples in each sample portion trough with the laser scanning cytometer over a fixed known area by fixing an extent scanned by the laser scanning cytometer that is digitized and keeping track of the number of known step-size steps that are moved in a perpendicular direction to complete the assay;
   iii) calculating a volume of the assay; and
   iv) thereby determining an absolute count and an undiluted absolute count of scanned cells in each sample portion trough.

3. The method of claim 1, wherein the method further comprises the steps of:
   i) precisely diluting the fluid test sample prior to placement in said reservoir;
   ii) performing an assay by determining the depth of each of the sample portion troughs;
   iii) scanning the fluid test samples in each sample portion trough with the laser scanning cytometer over a fixed known area by fixing an extent scanned by the laser scanning cytometer that is digitized and keeping track of the number of known step-size steps that are moved in a perpendicular direction to complete the assay;
   iv) calculating a volume of the assay; and
   v) thereby determining an absolute count and an undiluted absolute count of scanned cells in each sample portion trough.

4. The method of claim 3, wherein the depth of each trough is determined by separately focussing a laser of the laser scanning cytometer on indicia printed on two inner surfaces of each trough which define the depth of the trough and measuring the distance between focus points so obtained.

* * * * *

UNITED STATES PATENT AND TRADEMARK OFFICE
CERTIFICATE OF CORRECTION

PATENT NO. : 6,165,739　　　　　　　　　　　　　　　　　　　　　　Page 1 of 1
DATED : December 26, 2000
INVENTOR(S) : Clatch It is certified that error appears in the above-identified patent and that said Letters Patent is hereby corrected as shown below:

Title Page,
In the section entitled "Related U.S. Application Data," on the second line of the paragraph in that section, replace "08/614,649" with -- 08/614,469 --.
In the section entitled "Related U.S. Application Data," on the third line of the paragraph in that section, replace "Pat. No. 5,889,913" with -- abandoned --.

Column 1,
Line 7 replace "U.S. Pat. No. 5,889,913" with -- abandoned --.

Column 8,
Line 51 delete "meaningfully".

Column 10,
Line 6 replace "focussing" with -- focusing --.

Signed and Sealed this

Ninth Day of October, 2001

Attest:

NICHOLAS P. GODICI
Attesting Officer　　　Acting Director of the United States Patent and Trademark Office